United States Patent [19]

Sacchettini et al.

[11] Patent Number: 5,554,522

[45] Date of Patent: Sep. 10, 1996

[54] DIHYDRODIPICOLINATE REDUCTASE CRYSTALS AND THREE DIMENSIONAL STRUCTURE

[75] Inventors: James Sacchettini, New Rochelle; John Blanchard, Pelham Manor, both of N.Y.

[73] Assignee: Albert Einstein College of Medicine of Yeshiva University, a Division of Yeshiva University, Bronx, N.Y.

[21] Appl. No.: 234,135

[22] Filed: Apr. 28, 1994

[51] Int. Cl.[6] ................................................ C12N 9/02
[52] U.S. Cl. ................................................ 435/189
[58] Field of Search ................................................ 435/189

[56] References Cited

U.S. PATENT DOCUMENTS 4,833,233  5/1989  Carter ...................................... 530/363

OTHER PUBLICATIONS

Varughese et al., Proc. Natl. Acad. Sci, USA, vol. 89, 6080–6084, 1992.
Goldberg et al., J. Mol. Biol., 225, 909–911, 1992.
Lu et al., J. Mol. Biol., 224, 277–279, 1992.
Cuemer et al., J. Gen. Micro., 134, 3221–3229, 1988.
Laber et al., BC PC Monogr., '42 (Prospects Amino Acid Biosynth. Inhib. Crop Prot. Pharm. Chem.) pp. 81–83, 1989.
Bonner et al., Methods Plant Biochem., 3, 297–313, 1990.
Cheremisinoff et al., *Biotechnology: Applications & Research*, pp. 545–546, 1985.

*Primary Examiner*—Michael G. Wityshyn
*Assistant Examiner*—Jean C. Witz
*Attorney, Agent, or Firm*—Amster, Rothstein & Ebenstein

[57] ABSTRACT

This invention relates to dihydrodipicolinate reductase crystals and to methods of growing said crystals. This invention is further directed to the utilization of said crystals to determine the three dimensional structure of dihydrodipicolinate reductase. Compounds which inhibit the activity of dihydrodipicolinate reductase in bacteria and in plants can be developed utilizing the three dimensional structure of dihydrodipicolinate reductase.

6 Claims, 7 Drawing Sheets

PROPOSED CHEMICAL MECHANISM FOR THE REACTION CATALYZED BY DIHYDRODIPICOLINATE REDUCTASE

DIHYDRODIPICOLINATE REDUCTASE CRYSTALS AND THREE DIMENSIONAL STRUCTURE

STATEMENT OF GOVERNMENT INTEREST

This invention was made with government support under NIH Grant Number AI33696. As such, the government has certain rights in this invention.

FIELD OF THE INVENTION

This invention is directed to dihydrodipicolinate reductase crystals and to the three dimensional structure of said crystals. Specifically, this invention is directed to dihydrodipicolinate reductase crystals suitable for x-ray diffraction studies and to a method of producing said dihydrodipicolinate reductase crystals. The crystals are used to determine the three dimensional structure of dihydrodipicolinate reductase. The three dimensional structure of dihydrodipicolinate reductase allows for the development of compounds which inhibit the biochemical activity of dihydrodipicolinate reductase in bacteria and plants. These compounds are administered to treat bacterial infection or as herbicides.

BACKGROUND OF THE INVENTION

Dihydrodipicolinate reductase (DHPR) is an enzyme constituent of the diaminopimelate-lysine pathway in bacteria and plants. It is a 273 residue polypeptide, with a molecular weight of about 28,000 Da, and has been shown to exist as a tetramer of identical subunits. The enzyme catalyzes the NADPH or NADH-dependent reduction of dihydrodipicolinate:

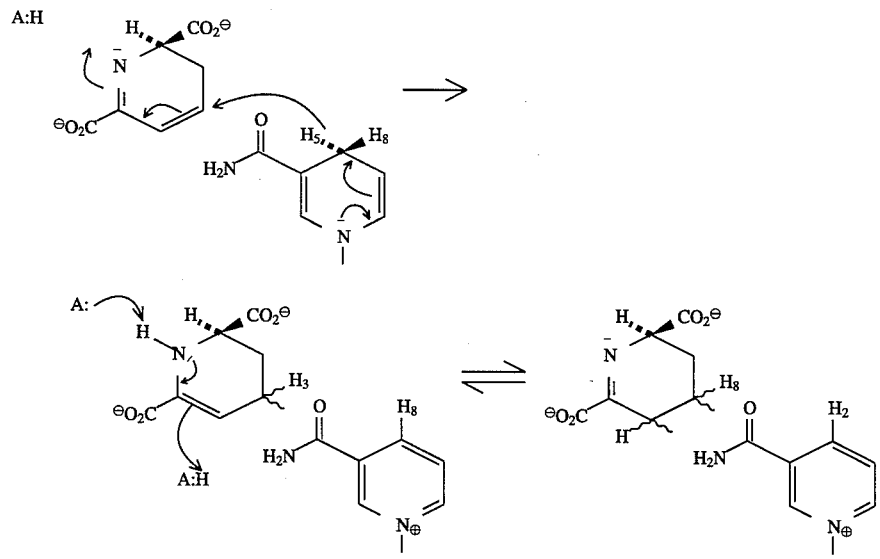

Diaminopimelic acid (DAP) is an essential component of the peptidoglycan layer of bacterial cell walls, and disruption of its biosynthesis results in cell death, most probably due to instability of the peptidoglycan. Nine enzymes, including dihydrodipicolinate reductase, are involved in the biosynthesis of DAP. The presence of these enzymes is essential for the survival of bacteria and plants. These enzymes are absent in mammalian cells.

There are three known pathways for the biosynthesis of DAP utilized by bacteria (see FIG. 1). They have been designated as the succinylase, dehydrogenase and acetylase pathways. Different bacteria utilize one or more of the three pathways. For example, *Escherichia coli* synthesizes DAP predominantly via the succinylase pathway; Bacillus species show a great deal of variability in DAP biosynthesis, and the dehydrogenase and acetylase pathways appear to be the most common; and Corynebacterium species appear to utilize all three of the pathways. This redundancy may indicate the importance of the DAP biosynthesis for bacterial survival.

In the last few years, an increasing number of bacteria have developed drug resistance to many commonly used antibiotics, such as streptomycin, β-lactams, isoniazid and ethionamide, thereby contributing to a new spread of disease. The search for new antibacterial drugs has consequently increased in importance. The nine enzymes of the DAP biosynthetic pathway represent excellent targets for the development of novel anti-bacterial and herbicidal agents, since no presently used antibiotics or herbicides target enzymes in this pathway. Inactivation of any of the enzymes would result in cell death. Inactivation of dihydrodipicolinate reductase will eliminate viability of bacteria and plants, since its product (THP) is a precursor of all of the three pathways.

It is desirable to know the three dimensional structure of dihydrodipicolinate reductase in order to develop compounds (drugs or herbicides) which inhibit the biochemical activity of this enzyme. If dihydrodipicolinate reductase crystals suitable for x-ray diffraction studies are produced, then the three dimensional structure of dihydrodipicolinate reductase can be determined. Obtaining the three dimensional structure of dihydrodipicolinate reductase would enable understanding the interactions between the enzyme (dihydrodipicolinate reductase) and substrates, which would enable those skilled in the art to utilize rational mechanism-based and structure-based drug design technology to develop specific inhibitors that would function as novel antibiotic drugs and herbicides.

It is therefore an object of this invention to provide dihydrodipicolinate reductase crystals which can be used to determine the three dimensional structure of dihydrodipicolinate reductase.

It is another object of this invention to provide methods of producing dihydrodipicolinate reductase crystals.

It is a further object of this invention to provide isolated dihydrodipicolinate reductase.

It is a still further object of this invention to provide a method of determining the three dimensional structure of dihydrodipicolinate reductase.

It is another object of this invention to provide the three dimensional structure of dihydrodipicolinate reductase, which structure can be used to develop bacteriocides and herbicides.

SUMMARY OF THE INVENTION

This invention is directed to dihydrodipicolinate reductase crystals and to methods of growing said crystals. This invention is further directed to the three dimensional structure of dihydrodipicolinate reductase, a method of determining such structure and the use of said three dimensional structure to develop compounds which inhibit the biochemical activity of dihydrodipicolinate reductase in bacteria and plants.

This invention provides dihydrodipicolinate reductase binary crystals in the form of parallelepipeds having the space group I222, a size of about 0.5×0.5×1.5 mm and unit cell constants of a=75.3 Å; b=81.5 Å; c=94.2 Å; and $\alpha=\beta=\gamma=90.0°$, wherein said crystals are suitable for x-ray diffraction to at least 2.5 Å resolution. This invention further provides for dihydrodipicolinate reductase ternary crystals in the form of parallelepipeds or diamonds having the space group $P2_12_12_1$ A which are suitable for x-ray diffraction to at least 3.0 Å resolution having the unit cell constants a=138.4 Å; b=123.4 Å; c=67.1 Å; and $\alpha=\beta=\gamma=90.0°$. Where the ternary crystals are in the form of parallelepipeds, they have a size of about 0.6×0.5×0.4 mm. Where the ternary crystals are in the form of diamonds, they have a size of about 1.0×0.5×0.1 mm.

This invention further provides for a method of producing dihydrodipicolinate reductase crystals comprising providing a solution containing dihydrodipicolinate reductase, providing a precipitant solution, mixing a droplet of dihydrodipicolinate reductase solution with a droplet of precipitant solution to obtain a mixed droplet solution, suspending the mixed droplet solution over a well of precipitant solution in a sealed container wherein the vapor pressure of the precipitant solution is lower than the vapor pressure of the mixed droplet solution, and allowing the mixed droplet solution to stand for a period of time sufficient for dihydrodipicolinate reductase crystals to grow to a predetermined size.

This invention is further directed to an isolated dihydrodipicolinate reductase enzyme comprising a first domain containing six α-helices and seven β-strands, a second domain containing two α-helices and four long β-strands and first and second loops connecting said first and second domains. Additionally, this invention is directed to a method of determining the three dimensional structure of dihydrodipicolinate reductase.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein.

DETAILED DESCRIPTION OF THE INVENTION

Figure 1:
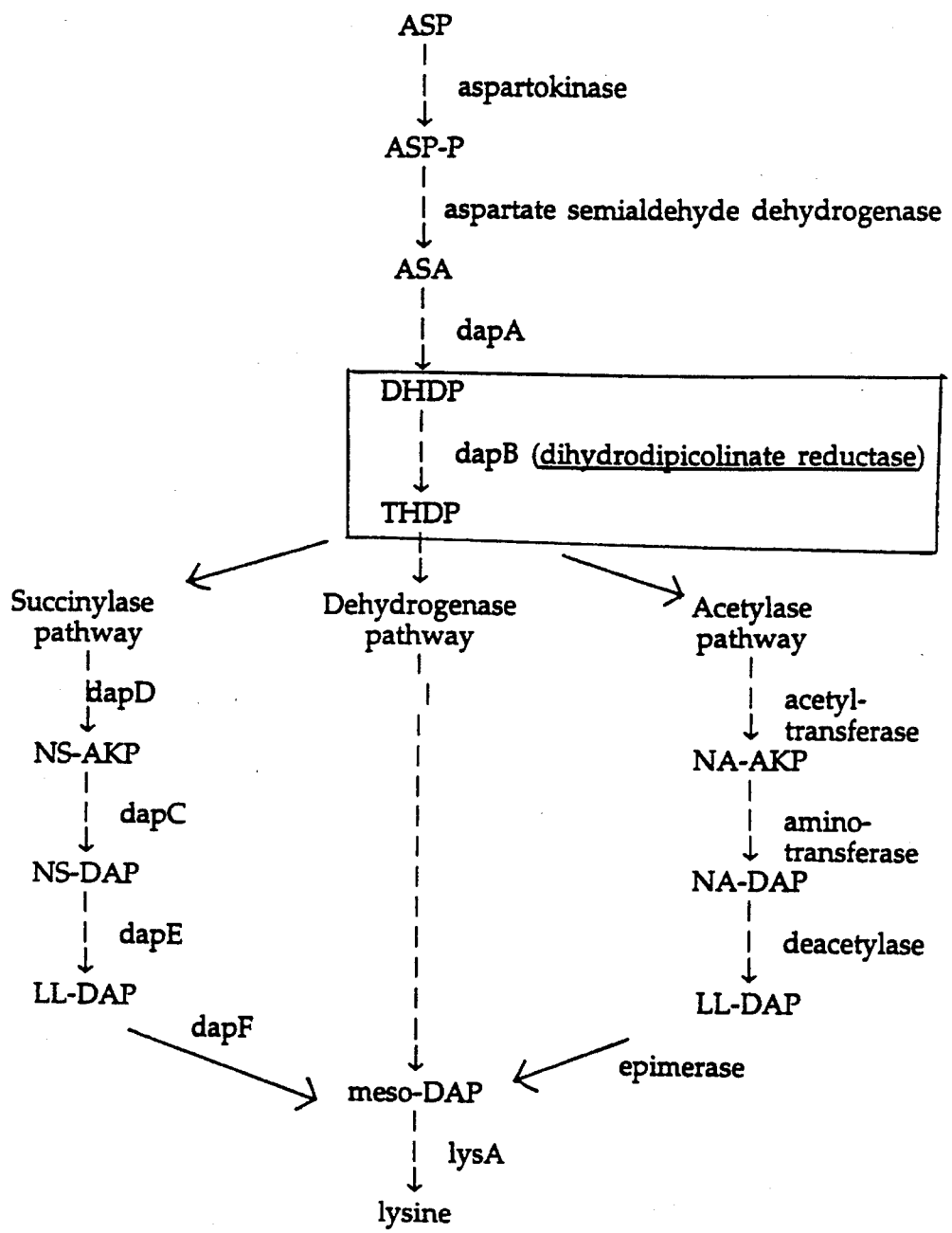
FIG. 1 represents three described pathways for the biosynthesis of diaminopimelic acid.
Figure 2:
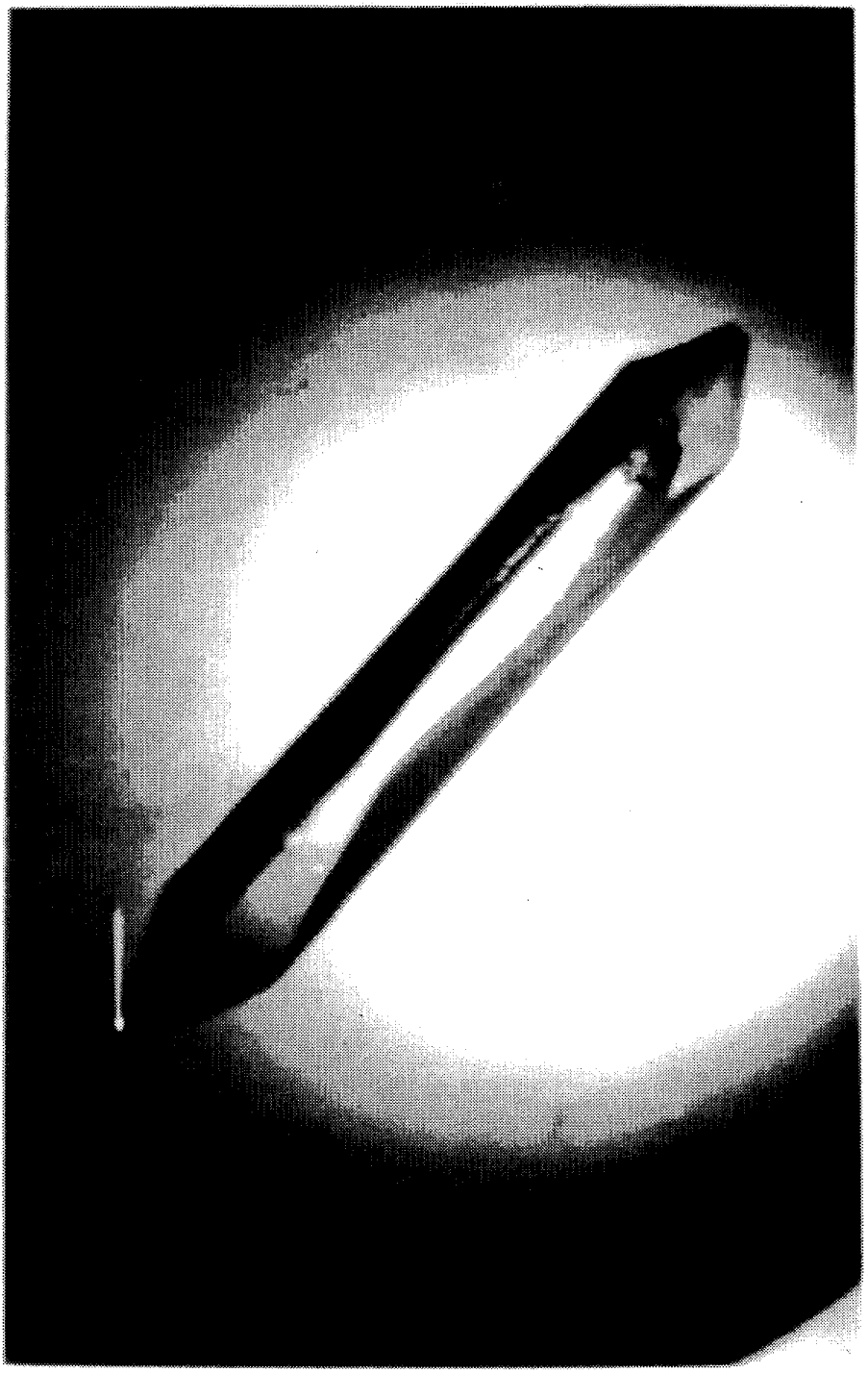
FIG. 2 represents a photograph of a crystal of the binary NADPH-dihydrodipicolinate reductase complex.
Figure 3:
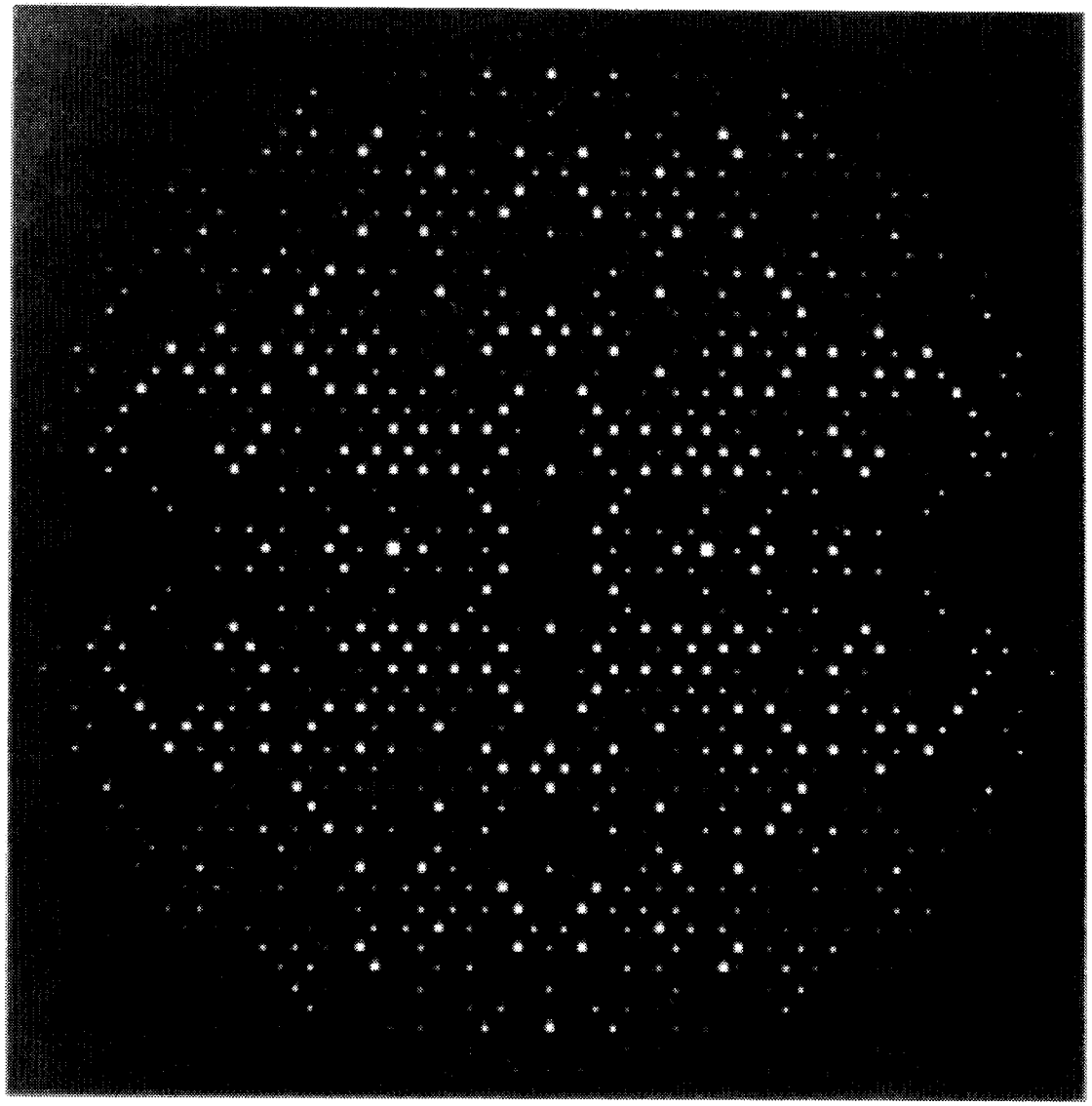
FIG. 3 represents a computer-generated precession photograph of a crystal of the binary NADPH-dihydrodipicolinate reductase complex.
Figure 4:
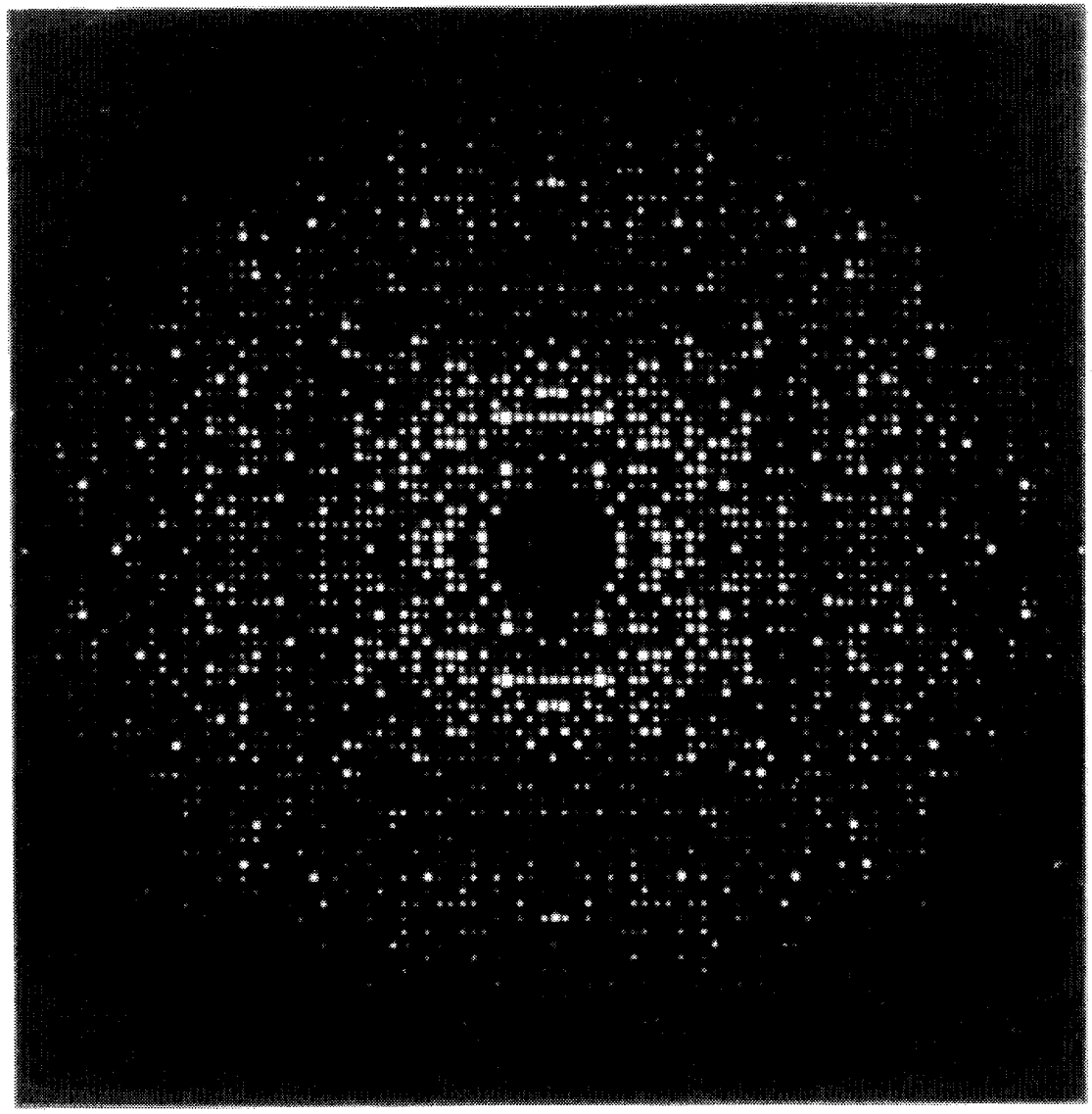
FIG. 4 represents a computer-generated precession photograph of a crystal of the ternary NADPH-PDC-dihydrodipicolinate reductase complex.

This invention is directed to dihydrodipicolinate reductase crystals and the methods of making said crystals. Said crystals are used to determine the three dimensional structure of dihydrodipicolinate reductase and its binary and ternary complexes, and to methods of determining the three dimensional structure of dihydrodipicolinate reductase and its binary and ternary complexes. The three dimensional structures of dihydrodipicolinate reductase and its binary and ternary complexes allow for the development of compounds which block the biochemical activity of dihydrodipicolinate reductase. These compounds, when put into contact with bacteria or plants, inhibit the biosynthesis of tetrahydrodipicolinate and cause the bacteria or plant to die. As a result, these compounds can be administered to treat bacterial infection, or to act as herbicides.

In order to produce dihydrodipicolinate reductase crystals, a solution containing dihydrodipicolinate reductase is provided, and a precipitant solution containing ammonium sulphate and a buffer is also provided. Dihydrodipicolinate reductase can be obtained by expressing the gene encoding dihydrodipicolinate reductase and purifying the dihydrodipicolinate reductase protein using standard techniques known to those skilled in the art. The dihydrodipicolinate reductase utilized to make crystals as described herein is from *E. coli*, but can be from any source, including *M. tuberculosis*. A droplet of dihydrodipicolinate reductase solution is mixed with a droplet of precipitant solution to obtain a mixed droplet solution. The mixed droplet solution is suspended over a well of precipitant solution in a sealed container. The vapor pressure of the precipitant solution in the well must be lower than the vapor pressure of the mixed droplet solution in order for crystals to form. The mixed droplet solution is allowed to stand for a period of time sufficient for dihydrodipicolinate reductase crystals to reach a predetermined size.

Preferably, the buffer used in this method is HEPES. The ammonium sulphate has a concentration of between 2.0 and 2.4M, and preferably has a concentration of 2.2M. The buffer may have a concentration of 100 mM, and the dihydrodipicolinate reductase, if in aqueous solution, has a concentration of between 12 and 18 mg/ml, and preferably has a concentration of 18 mg/ml. In addition, the pH of the dihydrodipicolinate reductase solution is about 7.5.

In order to form dihydrodipicolinate reductase binary crystals, dihydrodipicolinate reductase is mixed with a 1.5 fold molar excess of NADPH. Dihydrodipicolinate reductase crystals or binary complex crystals are in the form of parallelepipeds, have the space group I222 and have the following unit cell constants: a=75.3 Å; b=81.5 Å; c=94.2 Å; and $\alpha=\beta=\gamma=90.0°$. The dihydrodipicolinate reductase binary crystals have a size of about 0.5×0.5×1.5 mm, and are suitable for x-ray diffraction to at least 2.5 Å resolution. For dihydrodipicolinate reductase binary crystals, precession photographs show the presence of reflections for h or k or l=2n in the h00, 0k0 and 00l zones, for k+l or h+l or h+k=2n in the 0kl, h0l and hk0 zones and for h+k+l=2n in the hkl zone. This pattern is consistent with space group I222.

Dihydrodipicolinate reductase ternary crystals can be produced by mixing dihydrodipicolinate reductase with a 1.5 molar excess of NADPH and a 2.5 molar excess of 2,6-pyridinedicarboxylate (PDC) for 30–45 minutes at 4° C. to obtain a ternary complex of NADPH, PDC and dihydrodipicolinate reductase. Next, a precipitant solution containing polyethylene glycol, a salt and a buffer is provided. A droplet of dihydrodipicolinate reductase solution is mixed with a droplet of precipitant solution to obtain a mixed droplet solution. The mixed droplet solution is suspended over a well of precipitant solution in a sealed container. The vapor pressure of the precipitant solution in the well must be lower than the vapor pressure of the mixed droplet solution. The mixed droplet solution is allowed to stand for a period of time sufficient for dihydrodipicolinate reductase ternary crystals to grow to a predetermined size. Crystals appear in one to three weeks.

Preferably, the polyethylene glycol has a molecular weight of between 4,000 and 8,000, and has a concentration of 23–33% weight:volume. Best results are obtained where the polyethylene glycol is at a concentration of 30% weight:volume. The buffer has a concentration of 100 mM. Where the buffer is sodium citrate, the buffer has a pH of 5.6. Where the buffer is sodium cacodylate, the buffer has a pH of 6.5. The salt for the precipitant solution may be selected from the group consisting of ammonium acetate, ammonium sulphate and sodium acetate.

The dihydrodipicolinate reductase ternary crystals are in the form of parallelepipeds or diamonds, and have the space group $P2_12_12$, and have the following unit cell constants: a=138.4 Å; b=123.4 Å; c=67.1 Å; and $\alpha=\alpha=\gamma=90.0°$. Where the ternary crystals are in the form of parallelepipeds, the crystals have a size of about 0.6×0.5×0.4 mm. Where the crystals are in the form of diamonds, they have a size of about 1.0×0.5×0.1 mm. The ternary crystals are suitable for x-ray diffraction to at least 3.0 Å resolution. For ternary crystals, there is a tetramer per asymmetric unit. In precession photographs, reflections for h or k or l=2n are present in the h00,0k0 and 00l zones, indicating a $P2_12_12_1$ space group.

One method which can be used to solve the three-dimensional structure of dihydrodipicolinate reductase is multiple isomorphous replacement (MIR). X-ray diffraction data collected from heavy atom derivatives of the native protein are used to produce initial phases and electron density maps. Two heavy atom derivatives are used in the dihydrodipicolinate reductase structure determination. The first, ethylmercury phosphate (EMP) is obtained by soaking overnight (8 to 12 hours) a protein crystal in a solution containing 1 mM EMP in 100 mM HEPES, pH=7.5, 2.2M ammonium sulphate. Two heavy atom molecules per molecule of protein are thus introduced. The second derivative, mercury acetate (MA) may be obtained by soaking a native protein crystal in a solution containing 0.25 mM MA in the same buffer as above. One single heavy atom molecule, in a position different from the two obtained with EMP, is introduced. Isomorphous x-ray diffraction data from both derivatives, coupled with anomalous data from the MA derivative, allow for unambigous phasing of the protein data. The resulting electron density map allows for the tracing of the complete main chain and the insertion of the complete amino acid sequence of dihydrodipicolinate reductase, minus the first four residues, for which no electron density was visible.

The three-dimensional structure of the ternary complex DHPR:NADPH:PDC may be solved using molecular replacement procedures, with a monomer or dimer of the DHPR or DHPR:NADPH complex as a searching model. A rigid body fitting is used to discriminate between solutions of the rotation function. Two unique solutions are eventually found, and translation searches are run separately using both solutions to give the final models.

The inventors have determined that dihydrodipicolinate reductase is a two-domain protein, of an elongated shape, measuring approximately 65×35×38 Å. The first domain contains 6 α-helices (of which 5, A1 through A5, belong to the N-terminal portion of the protein, and one, A8, belongs to the C-terminal region) and 7 β-strands (six, B1 through B6, formed by residues of the N-terminus and one, B11, formed by residues of the C-terminus). These secondary structural elements are arranged to form an α/β structure similar to the dinucleotide binding domains of many dehydrogenases: the 6+1 β-strands are located in the middle, forming a twisted β-sheet surrounded by the helices. A sharp loop connects the first to the second domain of dihydrodipicolinate reductase. This domain contains two α-helices (A6 and A7) and 4 long β-strands (B7 through B10), which form an open mixed beta sandwich, since it contains mixed parallel (B7 and B8) and antiparallel (B7, B9 and B10) β-strands. Another loop connects B10 and A8 which belongs to the first domain. The last 10 residues form a distorted α-helix that is almost parallel to A6.

Dihydrodipicolinate reductase is a tetrameric protein, and analysis of the crystal packing of the protein in the I222 space group shows the presence of a possible tetramer, generated by crystallographic symmetry operators. The interactions between The monomers are located mainly in the C-terminal domains, where the 4 β-strands of one monomer are parallel with the 4 β-strands of a second to form a 8-stranded β-sheet. The second β-sheet, formed by the other two monomers of the tetramer, lies almost perpendicular to the first. The C-terminal domains thus form the core of the tetramer, and the four N-terminal domains extend from the core to the outside.

Figure 5:
FIG. 5 represents the three dimensional structure of the binary NADPH-dihydrodipicolinate reductase complex.
Figure 6:
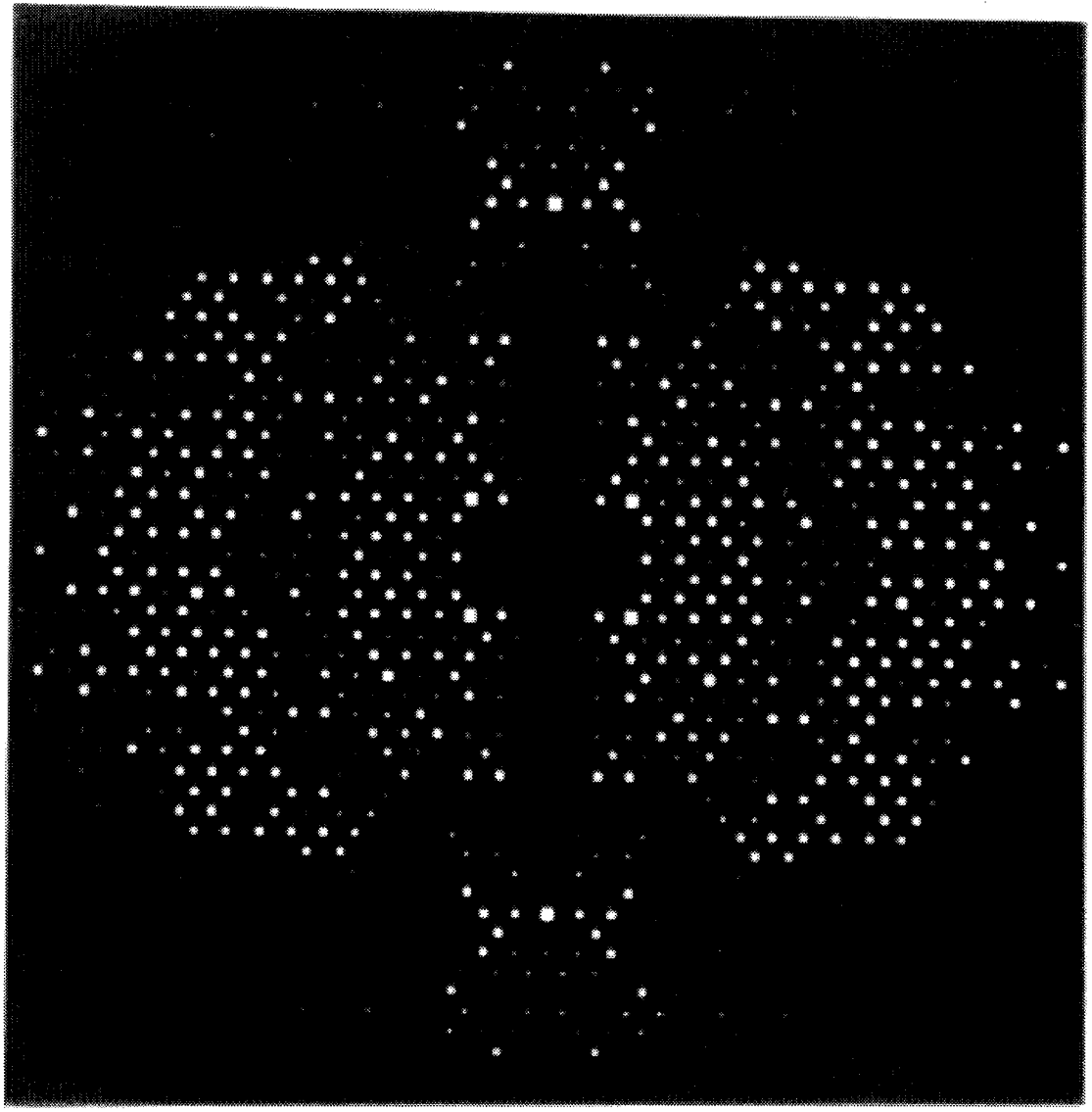
FIG. 6 represents a computer-generated precession photograph of a crystal of uncomplexed dihydrodipicolinate reductase.
Figure 7:
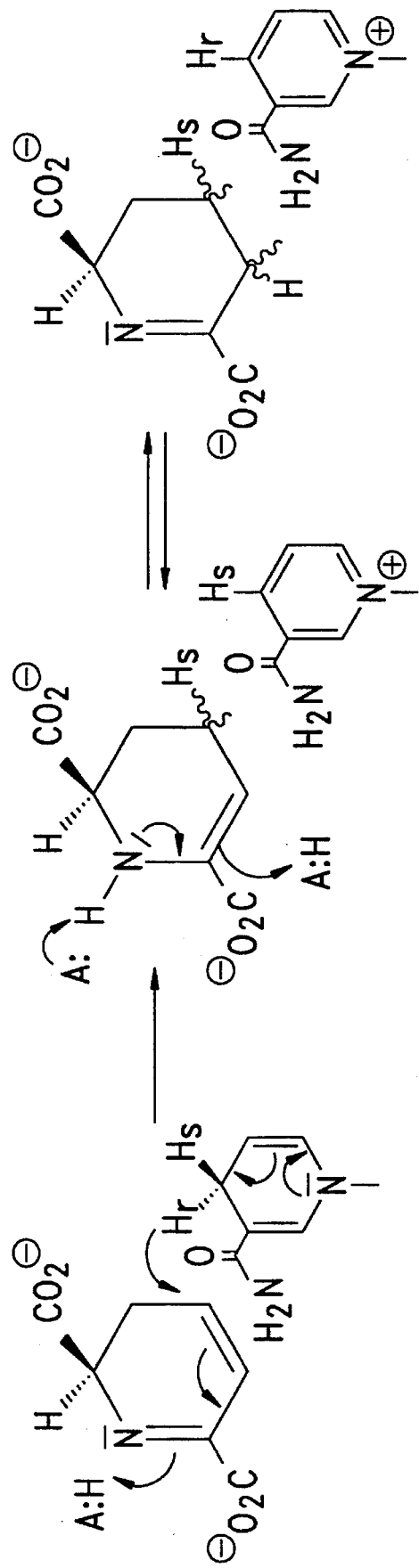
FIG. 7 represents the chemical mechanism of dihydrodipicolinate reductase.

Location of the bound cofactor, NADPH, can easily be achieved using a difference Fourier electron density map, calculated between the data collected from a crystal of unliganded dihydrodipicolinate reductase and data collected from a binary complex crystal. NADPH is located in an extended conformation across the C-terminal portion of the β-sheet of the first domain. The nicotinamide portion of the colactor shows an extensive network of hydrogen bonds with the protein, while the adenine portion is rather loosely bound, as confirmed by the somehow weaker electron density found for this portion of NADPH. The nicotinamide ring is located within a tight pocket formed by the protein's atoms, and this defines the stereospecificity of hydrogen transfer to the substrate, dihydrodipicolinate, by dihydrodipicolinate reductase. The enzyme can be thus classified as a pro-R specific dehydrogenase/reductase. The nicotinamide C4 atom faces the interface of the two domains (as seen in FIG. 5). Adjacent to the nicotinamide ring, a cluster of positively charged residues (His159, His160, Arg161, His162 and Lys163) is found. Given the negative charge of the protein's substrate, dihydrodipicolinate, and the nearby nicotinamide ring, this region represents the substrate and inhibitor binding site.

With the three dimensional structure and chemical mechanism of dihydrodipicolinate reductase defined, compounds which inhibit its biochemical activity can be designed and produced. When such compounds are put into contact with dihydrodipicolinate reductase, dihydrodipicolinate reductase cannot produce tetrahydrodipicolinate, a precursor of diaminopimelate, an essential component of the peptidoglycan layer of bacterial cell walls. Such compounds would also prevent the synthesis of L-lysine in plants. This would result in death of the bacteria or plant. Hence, compounds which inhibit the biochemical activity of dihydrodipicolinate reductase are administered to treat bacterial infection or as herbicides. In the case of bacterial infection, such compounds can be administered orally, enterally, intraperitoneally, subcutaneous, intravenously or by other modes known to those skilled in the art. As herbicides, such compounds can be administered by spreading or spraying.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. An isolated dihydrodipicolinate reductase-NADPH crystallized complex in the form of a parallelepiped with a space group of I222, and having unit cell constants of a=75.3 Å, b=81.5 Å, c=94.2 Å, and $\alpha=\beta=\gamma=90°$.

2. The crystallized complex of claim 1, having a size of about 0.5×0.5×1.5 mm.

3. An isolated dihydrodipicolinate reductase-NADPH-PDC crystallized complex in the form of a parallelepiped with a space group of $P2_12_12_1$, and having unit cell constants of a=138.4 Å, b=123.4 Å, c=67.1 Å, and $\alpha=\beta=\gamma=90°$.

4. The crystallized complex of claim 3, having a size of about 0.6×0.5×0.4 mm.

5. An isolated dihydrodipicolinate reductase-NADPH-PDC crystallized complex in the form of a diamond with a space group of $P2_12_12_1$, and having unit cell constants of a=138.4 Å, b=123.4 Å, c=67.1 Å, and $\alpha=\beta=\gamma=90°$.

6. The crystallized complex of claim 5, having a size of about 1.0×0.5×0.1 mm.

* * * * *